US006313069B1

(12) United States Patent
Tsukamoto et al.

(10) Patent No.: US 6,313,069 B1
(45) **Date of Patent: *Nov. 6, 2001**

(54) **STRAIN BELONGING TO *EXSEROHILUM MONOCERAS*, AND USES THEREOF**

(75) Inventors: Hiroshi Tsukamoto; Michiyo Takabayashi; Tadaharu Hieda; Masatoshi Gohbara, all of Kanagawa (JP)

(73) Assignee: Japan Tobacco Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/875,079

(22) PCT Filed: Nov. 19, 1996

(86) PCT No.: PCT/JP96/03384

§ 371 Date: Jul. 17, 1997

§ 102(e) Date: Jul. 17, 1997

(87) PCT Pub. No.: WO97/19166

PCT Pub. Date: May 29, 1997

(30) Foreign Application Priority Data

Nov. 20, 1995 (JP) ..................................................... 7-301684

(51) Int. Cl.[7] ..................................................... A01N 63/04

(52) U.S. Cl. .......................... 504/117; 504/116; 504/118; 435/254.1; 424/274.1

(58) Field of Search .................................... 504/116, 117, 504/118; 435/254.1; 424/274.1

(56) References Cited

U.S. PATENT DOCUMENTS

| | | |
|---|---|---|
| 3,661,935 | 5/1972 | Aldridge et al. . |
| 4,775,405 | 10/1988 | Caulder et al. . |
| 4,808,207 | 2/1989 | Gotlieb et al. . |
| 5,332,573 | 7/1994 | Yamaguchi et al. . |
| 5,424,271 | 6/1995 | Yamaguchi et al. . |
| 5,434,121 | 7/1995 | Gohbara et al. . |
| 5,498,591 | 3/1996 | Gohbara et al. . |
| 5,498,592 | 3/1996 | Gohbara et al. . |
| 5,530,146 | 6/1996 | Arai et al. . |

FOREIGN PATENT DOCUMENTS

| | | |
|---|---|---|
| 605221A1 | 7/1994 | (EP) . |
| 2-35076 | 2/1990 | (JP) . |
| 5-65209 | 3/1993 | (JP) . |
| 06329513A | 11/1994 | (JP) . |
| WO95 17820 | 7/1995 | (WO) . |
| WO96 03882 | 2/1996 | (WO) . |

OTHER PUBLICATIONS

Alcorn, Mycotaxon 7 (2), 1978, 411–414.*

Zhang et al., Plant Disease, Sep. 1996, vol. 8, No. 9, p. 1053–1058.*

(List continued on next page.)

*Primary Examiner*—Laurie Scheiner

(57) ABSTRACT

The invention relates to a strain belonging to *Exserohilum monoceras* which shows the esterase zymogram pattern shown in FIG. 1, a weed-controlling agent containing the same, and a weed-controlling method using the same. The invention provides a novel strain belonging to *Exserohilum monoceras* excellent in herbicidal effects as well as in spore productivity.

8 Claims, 2 Drawing Sheets

ESTERASE ZYMOGRAM OF THE NOVEL STRAINS OF THE PRESENT INVENTION

OTHER PUBLICATIONS

Japanese Abstract JP–A–7079784, Mar. 28, 1995.
M.B. Ellis, Dematiaceous Hyphomycetes, pp. 402–453.
E.S. Luttrell, Pyrenophora, Cochliobolus & Setosphaeria, pp. 271–279.
J.L. Alcorn, Mycotaxon, vol. VII, No. 2, pp. 411–414, Jul.–Sep. 1978.
A Japanese language article, pp. 361–368.
A. Silvanesan, Mycological Papers, No. 158, Issued Nov. 10, 1987, pp. 211–212.
Y. Fujita et al., Ann. Phytopath. Soc Japan 56, 1990, pp. 273–275.
S. Gnanamanickam et al., Ann. Phytopath. Soc. Japan 58, 1992, pp. 380–385.
M. Iwano, Bull. Tohou Natl. Agric Exp. Stn, 75, p. 27–39 (1987).
ATCC Catalogue of Filamentous Fungi, 18$^{th}$ ed., pp. 159, 172, 173, 208, and 383.
K. Mori et al., Tetrahedron, vol. 45(6), pp. 1639–1646.
D.J. Robeson, Agric. Biol. Chem., vol. 46(11), pp. 2681–2683.
Leonard & Suggs, Mycologia, vol. 66, pp. 290–297.
J.M. Lenne et al., Plant Disease, vol. 74(12), pp. 945–951.
K.J. Leonard et al., Plant Disease, vol. 72(12), pp. 1034–1038.
Japanese Abstract #JP–A–3219883, Date: Sep. 27, 1991.
Japanese Abstract #JP–A–4360678, Date: Dec. 14, 1992.
Japanese Abstract #JP–A–4370090, Date: Dec. 22, 1992.
Japanese Abstract #JP–A–6277042, Date: Oct. 4, 1994.
Japanese Abstract #JP–A–7079784, Date: Mar. 28, 1995.
Database Cropu Online! P. Del Serrone, retrieved from STN–International, accession No. 1991–87334 Cropu, XP002140065, abstract & Phytoparasitica, vol. 19, No. 3, 1991, pp. 259–260.

* cited by examiner

ESTERASE ZYMOGRAM OF THE NOVEL STRAINS OF THE PRESENT INVENTION

ESTERASE ZYMOGRAM OF THE NOVEL STRAINS OF THE PRESENT INVENTION AND CONVENTIONAL STRAINS

STRAIN BELONGING TO *EXSEROHILUM MONOCERAS*, AND USES THEREOF

TECHNICAL FIELD

The present invention relates to a novel strain belonging to *Exserohilum monoceras*, a weed-controlling agent containing the same and a weed-controlling method using the same.

BACKGROUND ART

The use of agrochemicals is essential in farms for stable food production. However, a large amount of synthesized agrochemicals containing substances not found in nature are applied to land for a long period of time, thus bringing about harm. The most serious problem is their direct influences on human and domestic animals and their destruction of the ecological system. In recent years, the harmful influences on human and domestic animals have been reduced owing to drastic improvements in the specificity of agrochemicals for weeds, harmful insects and disease germs, but one should still pay adequate attention when coming into contact with a high concentration of agrochemicals in applying thereof. Further, the selectivity of agrochemicals for weeds, harmful insects and disease germs is not necessarily high, resulting often in disturbance of the ecological system.

To solve the problem, there is a need for development of pesticides not adversely affecting other species than the target species to protect the environment. One example of such pesticides is herbicides using weed pathogens. Certain weed pathogens are ubiquitous in weeds, and it is known that such pathogens can be used in a herbicide with little or no damage to humans, domestic animals, and small creatures including fishes, insects etc. and with less phytotoxicity on plants. Further, the specificity of such herbicides using pathogens for the target weed is so high that their selectivity is considered high and the ecological system is hardly disturbed. Examples of herbicides using weed pathogens commercially available at present are a herbicide DeVine using *Phytophthora palmivora* for Stranglervine, a herbicide Collego using *Colletotrichum gloeosporioides* f. sp. *aeschynomene* for Northern jointvetch, and a herbicide BioMal using *Colletotrichum gloeosporioides* f. sp. *malvae* for round-leaved mallow.

Examples of herbicides using weed pathogens for controlling Echinochloa spp. as the most serious weed in paddy fields are *Cochliobolus lunatus* (Anamorph: *Curvularia lunata*) [Weed Research, 27, 43–47, (1987) and Japanese Patent Application Laid-Open Publication No. 284,963/93], *Ustilago trichophora* [w093/05656], and *Drechslera monoceras* (synonym of *Exserohilum monoceras*) [Japanese Patent Application Laid-Open Publication Nos. 219,883/91, 226,905/92, 360,678/92, 370,090/92, 277,042/94, 329,513/94, and 247,822/94].

However, these conventional herbicides are disadvantageous:

for example, *Cochliobolus lunatus* needs dew period for more than 18 hours to demonstrate its sufficient effect; *Ustilago trichophora* needs 4 to 5 weeks after spraying until its sufficient effect appears; and *Drechslera monoceras* produces a small amount of spores. Therefore, herbicides using these fungi still have not come into practical use.

Problem for Solution by the Invention

The object of the present invention is to provide microorganisms having both a sufficient herbicidal effect and a high ability to produce spores.

DISCLOSURE OF THE INVENTION

The inventors screened strains pathogenic to Echinochloa spp. for a strain having a strong herbicidal effect, and found a group of strains having both a strong herbicidal effect and a high ability to produce spores. Further, the inventors examined these strains for their esterase zymogram pattern, and found that said group showed a similar esterase zymogram pattern not resembling any esterase zymogram patterns of known strains. On the basis of these findings, the inventors completed the following invention:

The present invention is a strain belonging to *Exserhilum monoceras* showing the esterase zymogram pattern shown in FIG. 1.

In addition, the present invention is a weed-controlling agent comprising said strain as the active ingredient.

Further, the present invention is a method of controlling weeds comprising use of said weed-controlling agent.

Hereinafter, the present invention is described in detail.

The strains of the present invention were isolated from diseased Echinochloa spp., and the fungal properties are as follows:

They are aerobic which form dark gray or black colonies on a potato sucrose agar medium plate. White or gray aerial mycelium may be observed. They bear a large number of dark conidia, each having about 2 to 8 septa and being spindle-shaped and widest in the middle and thin towards the ends. A hilum protrudes at the basal terminal. The conidium is about 40–150×10–25 μm in size.

From the above results, particularly the form and shape of their colonies and the morphology of their conidia, the inventors identified said strains as *Exserohilum monoceras* by referring to A. Sivanesan: "Graminicolous Species of Bipolaris, Curvularia, Drechslera, Exserohilum and Their Teleomorphs" (mycological Papers, No. 158, p. 261, Nov. 1987) pp. 201 to 237.

The genus designation "Exserohilum" follows the classification of A, Sivanesan. Luttrell (Revue de Mycologie,41, 271–279, (1977)) and Alcorn (Mycotaxon, 8, 411–414, (1978)) have also supported this classification. On the other hand, Ellis (Dematioceous Hyphomycetes, CMI, Kew, 608 (1971)) has classified the genera Exserohilum and Bipolaris as the genus Drechslera and he uses only the genus Drechslera. In recent years, however, there is no researcher other than Ellis who does not approve the genera Exserohilum and Bipolaris, so the adoption of the genus Exserohilum is considered appropriate. Because the teleomorph state of the genus Exserohilum is known to be the genus Setosphaeria, those microorganisms which are classified as the genus Setosphaeria can also be encompassed with in the scope of the present invention.

The strains of the present invention are specifically JTB-012, JTB-013, JTB-799, JTB-803, and JTB-808. JTB-012 has been deposited as FERM BP-5271, JTB-013 as FERM BP-5272, JTB-799 as FERM BP-5273, JTB-803 as FERM BP-5274, and JTB-808 as FERM BP-5275, all of which were deposited on Oct. 27, 1995 with the National Institute of Bioscience and Human-Technology, Agency of Industrial Science and Technology (1–3, Higashi 1-chome, Tsukuba-shi, Ibaraki-ken, Japan).

As shown in FIG. 2, these strains show an esterase zymogram pattern which is different from those of IF09800, IMI125854, IMI125855, ATCC24641, and ATCC58346 as known strains belonging to *Exserohilum monoceras.*

The culture of the present strains can be effected in the same manner as for known strains belonging to *Exserohilum*

*monoceras* without requiring any special method. The medium may be any synthetic or natural medium insofar as it suitably contains assimilative carbon and nitrogen sources and inorganic matter as well as a necessary growth promoter. Examples are oatmeal sucrose agar medium, oatmeal agar medium, potato sucrose agar medium, V-8 juice agar medium, Czapek-Dox agar medium, etc. During culture, the medium is maintained at a temperature of 15 to 30° C. , preferably 20 to 25° C., and at pH 3 to 9, preferably pH 5 to 8. After 7 to 14 days in culture under the above conditions, spores have been formed in a sufficient amount on the surface of the medium plate.

The weed-controlling agent of the present invention is prepared by adding surfactant etc. to said spores as the active ingredient. The density of spores can be arbitrarily determined within the range in which they demonstrate a herbicidal effect, where $10^2$ to $10^6$ spores/ml, preferably $10^3$ to $10^5$ spores/ml, can be suitably used.

For applying the weed-controlling agent of the present invention over an actual field, it is preferred to apply $10^9$ to $10^{10}$ spores/1000 $m^2$.

The weeds subject to the weed-controlling agent of the present invention include, but are not limited to, Echinochloa spp.

EXAMPLES

Example 1

Barnyard Grass (*Echinochloa crus-galli*) Control Test

Diseased plants belonging to Echinochloa spp. were collected from all over Japan. Their lesions were excised and incubated under humidity at 25° C., whereby conidia were formed. The conidia were scratched with a needle and inoculated onto a potato sucrose agar medium plate to separate single spores. Each strain was inoculated onto an oatmeal sucrose agar medium plate and cultured at 25° C. for 14 days to form conidia. Thereafter, the conidia were suspended in 0.02% aqueous Tween 20 at a density of $10^3$, $10^4$, and $10^5$ spores every 5 ml.

Separately, barnyard grasses were grown in a 100 $cm^2$ pot until the 1.5-leave stage, and water was flooded until water reached about 5 cm in depth. Five ml of each of said spore suspensions was added dropwise to each pot and allowed to stand for 3 weeks in a greenhouse and their herbicidal effect was examined. Their herbicidal effect on barnyard grasses was determined as follows:

Herbicidal Effect=[1−(Number of Survived Individuals/20)]×100

TABLE 1

Strains and Their Herbicidal Effect on Barnyard Grass

| | Herbicidal Effect | | |
|---|---|---|---|
| Strain | $10^3$ | $10^4$ | $10^5$ |
| JTB-012 | 38 | 95 | 100 |
| JTB-013 | 35 | 70 | 95 |
| JTB-799 | 47 | 100 | 100 |
| JTB-803 | 35 | 100 | 100 |
| JTB-808 | 32 | 100 | 100 |
| IMI-125855 | 0 | 2 | 25 |
| No Treatment | 0 | | |

Example 2

Conidia Productivity Test

Each strain was inoculated onto an oatmeal sucrose agar medium plate and grown in stationary culture at 25° C. for 14 days. Then, the conidia on the medium plate were recovered by suspending them in 0.1% Tween 20. The amounts of conidia produced are shown in Table 2.

TABLE 2

Strains and Their Production of Conidia

| Strain | Conidia Production/$cm^3$ |
|---|---|
| JTB-012 | $4.4 \times 10^5$ |
| JTB-013 | $4.5 \times 10^5$ |
| JTB-799 | $7.5 \times 10^5$ |
| JTB-803 | $8.6 \times 10^5$ |
| JTB-808 | $6.6 \times 10^5$ |
| IFO-9800 | $<2.4 \times 10^3$ |
| IMI-125854 | $<2.4 \times 10^3$ |
| IMI-125855 | $4.0 \times 10^4$ |
| ATCC-24641 | $<2.4 \times 10^3$ |
| ATCC-58346 | $<2.4 \times 10^3$ |

A group of the strains JTB-012, JTB-013, JTB-799, JTB-803 and JTP-808 produced at least $4.4\times10^5$ conidia/$cm^2$. On the other hand, the strain IMI-125855, i.e. having the highest ability to produce conidia among the known strains, produced $4.0\times10^4$ conidia/$cm^2$. The amount of conidia produced by every other known strain was below the limit of detection. This indicated that the amount of conidia produced by each member of the present group is 10 times greater than that of each of the known strains.

Example 3

Analysis of Esterase Zymogram

Ten strains JTB-012, JTB-013, JTB-799, JTB-803, JTB-808, IFO-9800, IMI-125854, IMI-125855, ATCC-24641 and ATCC-58346, were used as samples. The preparation of a crude enzyme solution from each strain was carried out by the method described in Japanese Patent Application Laid-Open Publication No. 329,513/94.

Each strain was grown in a potato sucrose liquid medium at 25 ° C. in the dark for 7 to 10 days by stationary to form a fungal mat. The mat was washed several times with distilled water, frozen at −80° C. and lyophilized.

The fungal mat was homogenized in 50 mM Tris-HCl buffer (pH 7.4) and filtered through a filter paper, and the filtrate was centrifuged at 10,000 r.p.m. The supernatant was used as a sample. The concentration of the sample protein was quantitatively determined by the Lowry method. Each sample, about 50$\mu$l protein, was electrophoresed at 30 mA for 2 hours using an acrylamide gel (concentration gel, 4.5%; separation gel, 10%) in a large slab gel electrophoresis.

After electrophoresis, staining of esterase activity was carried out. 40 mg of $\alpha$-naphthyl acetate was dissolved in 4 ml of 50% aqueous acetone, and 200 mg of fast violet B salt and 200 ml of 50 mM Tris-HCl buffer were added thereto, and the resulting solution was used as a staining solution. The gel was immersed in this staining solution and gently shaken for 30 minutes for staining. Thereafter, the gel was washed with distilled water and the mobility in each band was determined.

As a result, JTB-012, JTB-013, JTB-799, JTB-803 and JTB-808 indicated the same esterase zymogram pattern as shown in FIGS. 1 and 2, and thus it is evident that the strains JTB-012, JTB-013, JTB-799, JTB-803 and JTB-808 belong to the same group. Because the esterase zymogram pattern of the group of the present strains differs from those of the known strains IFO-9800, IMI-125854, IMI-125855, ATCC- 24641, ATCC-58346, and *Drechsrela monoceras* var. *microsporus* described in Japanese Patent Application Laid-Open Publication No. 329,513/94, it was evident that the group of the present strains is a group of novel strains different from the known strains.

FURMULATION EXAMPLES

Example 1

(Emulsion in Water)

$2\times10^9$ conidia of *Exserohilum monoceras* JTB-013 and 4 g of Tween 80 were added to 20 L of sterilized water, and they were mixed to prepare a liquid agent.

Example 2

(Wettable Powder)

Conidia (JTB-803) were suspended in a mixture of 9% maltose, 1% clay and 90% water to prepare a suspension containing $10^7$ conidia/ml. The suspension was air-dried, and the dried product was ground to prepare a wettable powder.

Example 3

(Wettable Powder)

Conidia (JTB-012) were suspended in a mixture of 9% lactose, 1% zeolite and 90% water to prepare a suspension containing $10^7$ conidia/ml. The suspension was air-dried, and the dried product was ground to prepare a wettable powder.

Example 4

(Wettable Powder)

Conidia (JTB-808) were suspended in a mixture of 15% diatomaceous earth, 77% kaolin and 8% polyoxyethylene alkylphenyl ether to prepare a suspension containing $10^7$ conidia/ml. The suspension was air-dried, and the dried product was ground to prepare a wettable powder.

Example 5

(Wettable Powder)

Conidia (JTB-799) were suspended in a mixture of 33% diatomaceous earth, 0.33% carboxymethylcellulose and 66.67% water to prepare a suspension containing $10^7$ conidia/ml. The suspension was air-dried, and the dried product was ground to prepare a wettable powder.

Example 6

(Dust)

Conidia (JTB-012) were mixed with a mixture of 14% hydroxypropyl-β-cyclodextrin, 12% white carbon and 74% clay to prepare a mixture containing $10^7$ conidia/g. The mixture was dried and homogeneously ground to prepare dust.

Example 7

(Granule)

Conidia (JTB-808) were kneaded with a mixture of 15% β-cyclodextrin, 2% starch, 18% bentonite, 36% potassium carbonate and 29% water to prepare a mixture containing $10^7$ conidia/g, which was then granulated in a granulating machine and dried to prepare a granular agent.

Example 8

(Emulsifiable Concentrate)

Conidia (JTB-799) were homogeneously suspended in a mixture of 18% polyoxyethylene nonylphenyl ether phosphate ammonium, 6% polyoxyethylene nonylphenyl ether, 29% triethyl phosphate and 47% tributyl phosphate to prepare an emulsion containing $10^7$ conidia/ml.

Example 9

(Oil Formulation)

Conidia (JTB-803) were suspended in a mixture of 95% spindle oil, 4% castor oil and 1% silicone oil to prepare an oily agent containing $10^7$ conidia/ml.

Example 10

(Dry Flowable)

Conidia (JTB-013) were suspended in a composition of 12% sodium alkylbenzene sulfonate and 88% polyethylene glycol ether to prepare a dry flowable agent containing $10^7$ conidia/mi.

Example 11

(Encapsulated Agent)

Conidia (JTB-803) were suspended in a mixture of 0.7% sodium alginate, 5% kaolin, 15% glycerin, and 79.3% water to prepare a suspension containing $10^7$ conidia/ml. The suspension was added dropwise onto 0.2 M calcium acetate to give a encapsulated product. This product was cut thin, sieved and air-dried to prepare a encapsulated agent.

Example 12

(Encapsulated Agent)

Conidia (JTB-013) were suspended in a mixture of 0.7% sodium alginate, 5% diatomaceous earth, 15% glycerin and 79.3% water to prepare a suspension containing $10^7$ conidia/ml. The suspension was added dropwise onto 0.2 M calcium chloride to give a encapsulated product. This product was cut thin, sieved and air-dried to prepare a encapsulated agent.

Effect of the Invention

The present invention provides a novel strain belonging to *Exserohilum monoceras*. The present strain is excellent in herbicidal effect and spore productivity as compared with conventional strains belonging to *Exserohilum monoceras*, and it has suitable properties as an ingredient in fungal herbicides.

Figure 1:
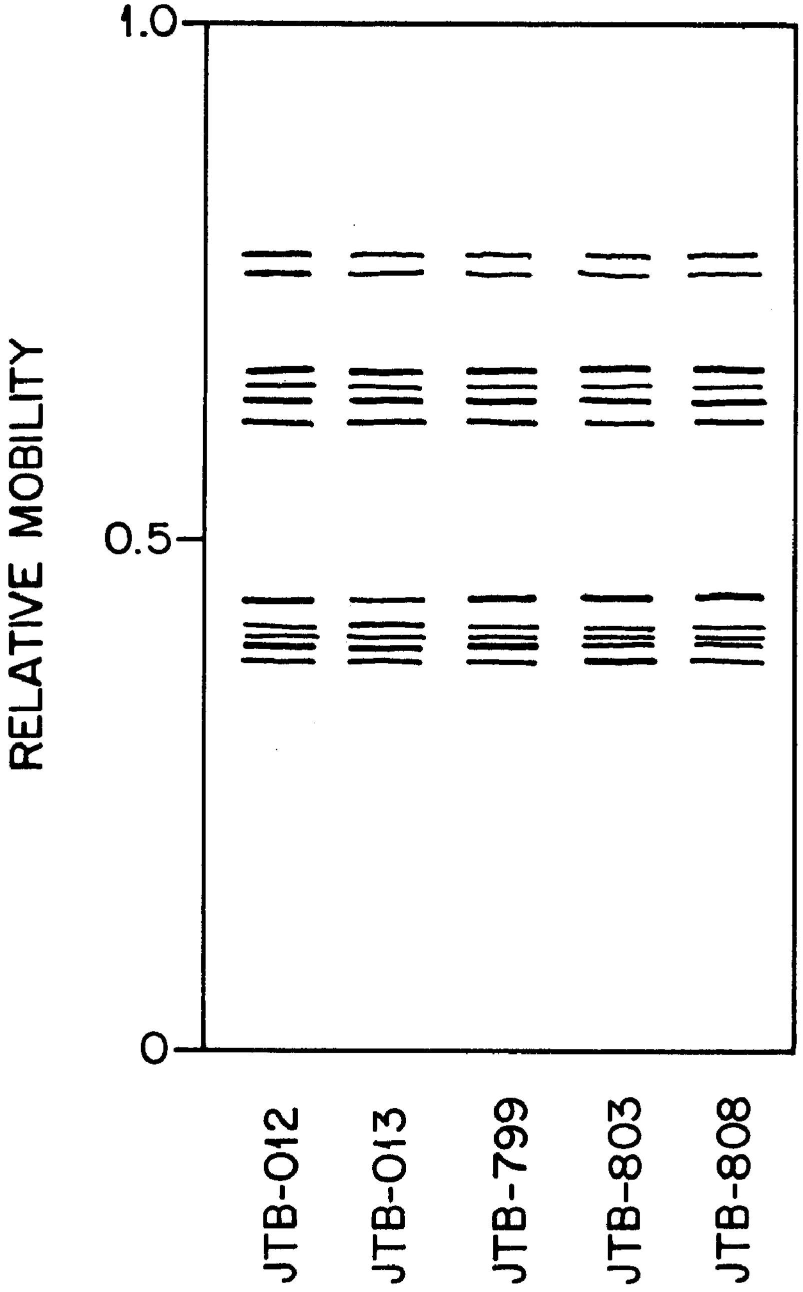
FIG. 1 is an esterase zymogram of the novel strains of the present invention.
Figure 2:
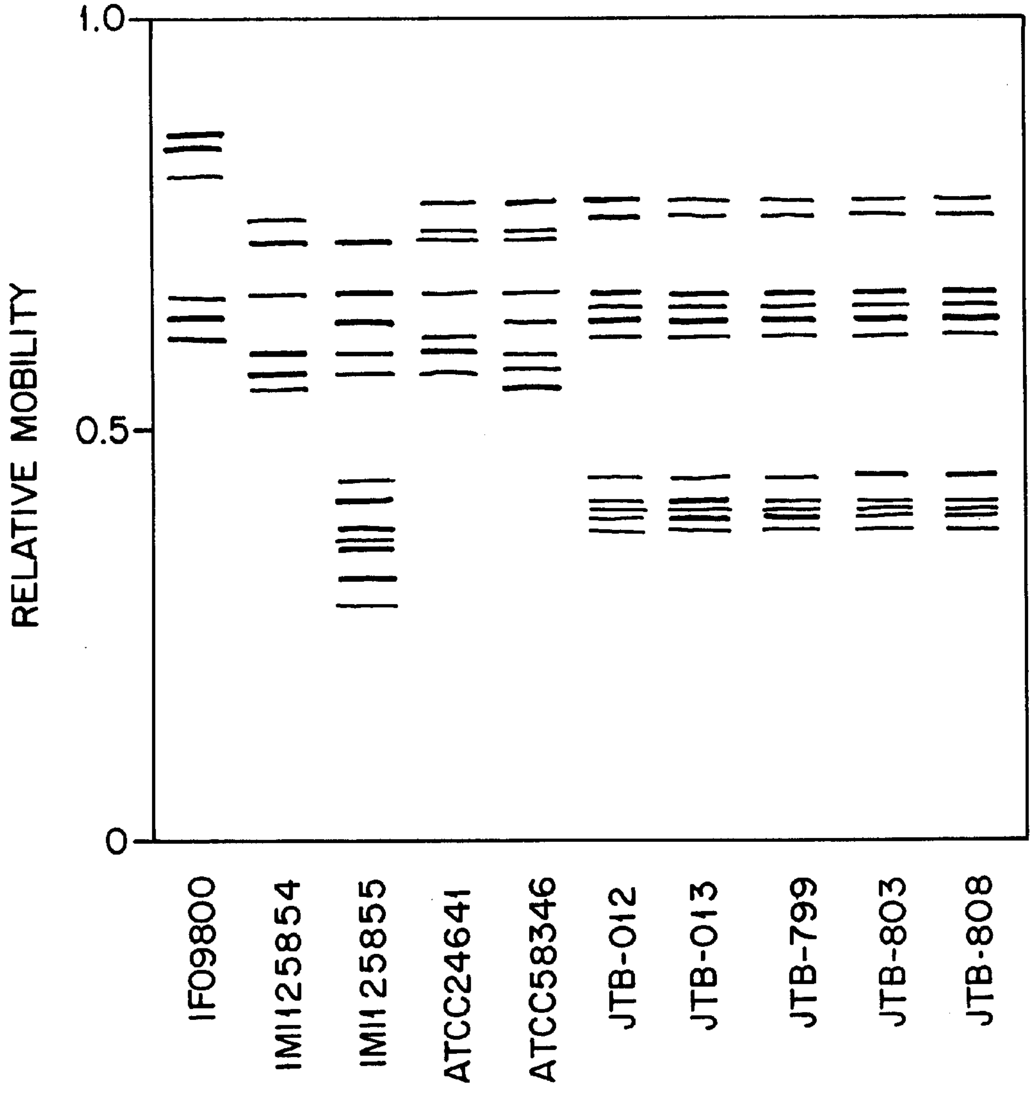
FIG. 2 is an esterase zymogram of the novel strains of the present invention and convention strains.

What is claimed is:

1. A strain belonging to *Exserohilum monoceras*, which shows the esterase zymogram pattern shown in FIG. 1 and is effective for controlling Echinochloa spp.

2. The strain according to claim 1, which is *Exserohilum monoceras* JTB-012, *Exserohilum monoceras* JTB-013, *Exserohilum monoceras* JTB-799, *Exserohilum monoceras* JTB-803, or *Exserohilum monoceras* JTB-808.

3. An agent for controlling weeds, which comprises the strain of claim 1 or 2 as the active ingredient.

4. The agent according to claim 3, wherein the weeds are Echinochloa spp.

5. A method for controlling weeds, which comprises using the agent of claim 3.

6. The method according to claim 5, wherein the weeds are Echinochloa spp.

7. The strain of claim 1, which is aerobic and forms gray or black colonies on a potato sucrose agar medium plate, white or gray aerial mycelium, dark conidia having about 2–8 septa and spindle-shaped and widest in the middle and thin toward the ends, a hilium protrudes at a basal terminal and the conidium is about 40–150×10–25 um in size.

8. The strain of claim 1, that produces at least $4.4\times10^5$ conidia/$cm^2$.

* * * * *